US006479053B1

(12) United States Patent
Jay (10) Patent No.: US 6,479,053 B1
(45) Date of Patent: Nov. 12, 2002

(54) LASER INACTIVATION OF INHIBITORY MOLECULES IN CENTRAL NERVOUS SYSTEM MYELIN

(75) Inventor: Daniel G. Jay, Brighton, MA (US)

(73) Assignee: President and Fellows of Harvard College

( * ) Notice: Subject to any disclaimer, the term of this patent is extended or adjusted under 35 U.S.C. 154(b) by 0 days.

(21) Appl. No.: 09/529,843

(22) PCT Filed: Oct. 23, 1998

(86) PCT No.: PCT/US98/22387

§ 371 (c)(1),
(2), (4) Date: Jun. 12, 2000

(87) PCT Pub. No.: WO99/20190

PCT Pub. Date: Apr. 29, 1999

Related U.S. Application Data (60) Provisional application No. 60/063,018, filed on Oct. 23, 1997.

(51) Int. Cl.[7] ............ A61K 39/40; A61K 39/42; A61K 39/44; A61K 39/395
(52) U.S. Cl. .................................................. 424/181.1
(58) Field of Search ...................................... 424/181.1

(56) References Cited

U.S. PATENT DOCUMENTS

| 4,966,144 A | 10/1990 | Rochkind et al. ........... 128/395 |
| 5,580,555 A | 12/1996 | Schwartz ................... 424/85.1 |
| 5,932,542 A * | 8/1999 | Filbin ............................ 514/8 |

OTHER PUBLICATIONS

PCT International Search Report for International Application No. PCT/US98/22387; Authorized Officer; Gucker, Stephen, Date of Completion: Mar. 15, 1999; Date of Mailing: Mar. 31, 1999 (3 Pages).

Aguayo, A.J. et al. (1991) "Degenerative and regenerative responses of injured neurons in the central nervous system of adult mammals". Phil. Trans. R. Soc. (London) B 331, 337–343.

Bartsch, U. et al. (1995) "Lack of Evidence That Myelin–Associates Glycoprotein is a Major Inhibitor of Axonal Regeneration in the CNS". Neuron 15, 1375–1381.

Beerman, A.E. et al. (1994) "Chromophore Assisted Laser Inactivation of cellar Proteins". Methods in Cell Biology 44, 716–732.

Bregman, B.S. et al. (1995) "Recovery from spinal cord injury mediated by antibodies to neurite growth inhibitors". Nature 378, 498–501.

Caroni, P. et al. (1988a) "Two Membrane Protein Fractions from Rat Central Myelin with Inhibitory Properties for Neurite Growth and Fibroblast Spreading". J. Cell Biol. 106, 1281–1288.

(List continued on next page.)

Primary Examiner—Gary Benzion
Assistant Examiner—Teresa Strzelecka
(74) Attorney, Agent, or Firm—Hale and Dorr LLP (57) ABSTRACT

Methods for specifically inactivating myelin proteins which inhibit nerve regeneration are described. These methods are useful to promote axon regeneration.

6 Claims, 3 Drawing Sheets

OTHER PUBLICATIONS

Caroni, P. et al. (1988b) "Antibody against Myelin–Associated Inhibitor of Neurite Growth Neutralizes Nonpermissive Substrate Properties of CNS White Matter". *Neuron 1*, 85–96.

Chang, H.Y. et al. (1995) "Asymmetric retraction of growth cone filopdia following focal inactivation of calcineuron". *Nature 376*, 686–690.

Cheng, H. et al. (1996) "Spinal Cord Repair in Adult Paraplegic Rats: Partial Restoration of Hind Limb Function". *Science 273*, 510–512.

Cox, E.C. et al. (1990) "Axonal Guidance in the Chick Visual System: Posterior Tectal Membranes Induce Collapse of Growth Cones from the Temproral Retina". *Neuron 4*, 31–37.

David, S. et al. (1981) "Axonal Elongation into Peripheral Nervous System "Bridges" After Central Nervous System Injury in Adult Rats". *Science 214*, 931–933.

Diamond, P. et al. (1993) "Fasciclin I and II Have Distinct Roles in the Development of Grasshopper Pioneer Neurons". *Neuron 11*, 409–421.

Hammerling, G.J. et al. "Production of Antibody–Producing Hybridomas in the Rodent Systems". *Monoclonal Antibodies and T–Cell Hybridomas*, Elsvier/North–Holland Biomedical Press, New York, NY, pp. 563–587.

Jay, D.G. (1988) "Selective destruction of protein function by chromophore–assisted laser inactivation". *Proc. Natl. Acad. Sci.* (USA) 85, 5454–5458.

Jay, D.G. et al. (1990) "Laser inactivation of fasciclin I disrupts axon adhesion of grasshopper pioneer neurons". *Nature 348*, 548–550.

Kohler, G. et al. (1975) "Continuous cultures of fused cells secreting antibody of predefined specificity". *Nature 256*, 495–497.

Liao, J.C. et al. (1996) "Chromophore–Assisted Laser Inactivation of Subunits of the T–Cell Receptor in living cells is spatially restricted". *Photochem. Photobiol. 62*, 923–929.

Liao, J.C. et al. (1994) "Chromophore–assisted laser activation of proteins is mediated by the photogeneration of free radicals". *Proc. Natl. Acad. Sci.* (USA) 91, 2659–2663.

McKerracher, L. et al. (1994) "Identification fo Myelin–Associated Glycoprotein as a Major Myelin–Derived Inhibitor of Neurite Growth". *Neuron 13*, 805–811.

Morrison, S.L. (1985) "Transfectomas Provide Novel Chimeric Antibodies". *Science 229*, 1202–1207.

Mukhopadhyay, G. et al. (1994) "A Novel Role for Myelin–Associated Glycoprotein as an Inhibitor of Axonal Regeneration". *Neuron 13*, 757–767.

Muller, B. et al. (1996) "Chromophore–assisted laser inactivation of a repulsive axonal guidance molecule". *Curr. Biol. 6*, 1497–1502.

Oi, V.T. et al. (1986) "Chimeric Antibodies". *BioTechniques 4*; 214–221.

Schafer, M. et al. (1996) "Disruption of the Gene for Myelin–Associated Glycoprotein Improves Axonal Regrowth along Myelin in C57BL/Wld$^s$ Mice". *Neuron 16*, 1107–1113.

Schnell, L. et al. (1990) "Axonal regeneration in the rat spinal cord produced by an antibody against myelin–associated neurite growth inhibitors". *Nature 343*, 269–272.

Schroder, R. et al. (1996) "Chromopore–assisted laser inactivation of even skipped in *Drosophila* precisely phenocopies genetic loss of function". *Dev. Genes Evol. 206*, 86–88.

Schwab, M.E. et al. (1993) "Inhibitors of neurite outgrowth". *Ann. rev. Neurosci. 16*, 565–595.

Sydor, A.M. et al. (1996) "Talin and Vinculin Play Distinct Roles in Filopodial Motility in the Neuronal Growth Cone". *J. Cell Biol. 134*, 1197–1207.

Wang, F.S. et al. (1996) "Chromophore–assisted laser inactivation (CALI): probing protein function in situ with a high degree of spatial and temporal resolution". *Trans Cell Biol. 6*, 442–445.

Weibel, D. et al. (1994) "Regeneration of lesioned rat optic nerve fibers is improved after neutralization of myelin–associated neurite growth inhibitors". *Brain Research 642*, 259–266.

* cited by examiner

FIG. 4

LASER INACTIVATION OF INHIBITORY MOLECULES IN CENTRAL NERVOUS SYSTEM MYELIN

This application claims benefit of a U.S. Provisional application no. 60/063,018 filed Oct. 23, 1997.

FIELD OF THE INVENTION

The invention relates to methods for specifically inactivating myelin proteins which inhibit nerve regeneration. These methods are useful to promote axon regeneration.

BACKGROUND OF THE INVENTION

Axon regeneration occurs from a severed end by forming a new neuronal growth cone, the sensory motile organelle at the ends of axons that is responsible for neurite extension and axon guidance of developing neurons. While central nervous system ("CNS") neurons do not regenerate after injury, peripheral nerves do. For example, severed nerves within the adult optic nerve generally do not regenerate (reviewed in Aguayo et al., 1991). It is thought that if the severed nerves reform circuitry, then significant function can be reestablished (Cheng et al., 1996).

David et al. (1981) showed that CNS nerves extended axons into bridges of peripheral tissue demonstrating that the difference between the CNS and peripheral nervous system environments is critical for regeneration. It has recently been shown that the major difference in regenerative capacity is due to inhibitory molecules present in the myelin sheaths that surround spinal cord axons of the adult CNS (Schwab et al., 1993). Spinal cord neurons show increased collateral sprouting when myelin is absent (Schwegler et al., 1995). Application of a myelin-derived fraction to neurons cultured in the absence of myelin caused growth cone collapse and neurite retraction (Caroni and Schwab, 1988a).

It has been demonstrated that at least one inhibitory property of myelin extracts can be partially neutralized by an antibody called IN-1 (Caroni and Schwab 1988b). The application of this antibody to injured rat spinal cord can promote a small amount of axon regeneration (Schnell and Schwab, 1990; Bregman et al., 1993). IN-1 also caused a small amount of regeneration after optic nerve lesion (Weibel et al., 1994). Regeneration was incomplete in these reported studies and in no case was reconnection made to former targets. This may have been due in part to the fact that IN-1 is only partially blocking (the antigen has yet to be purified). Also, there are several other inhibitory molecules present in the myelin, some that have yet to be identified (Schwab et al., 1993). Identifying these other molecules in myelin that inhibit regeneration would aid in developing treatment for CNS nerve injury.

Another neurite inhibitory protein derived from myelin (distinct from the IN-1 antigen) is the abundant myelin-associated glycoprotein (MAG) (McKerracher et al., 1994). Purified MAG can inhibit neurite outgrowth from peripheral sensory (DRG) neurons and neuroblastoma-derived cell lines such as NG-108 cells (McKerracher et al., 1994; Mukhopadhyay et al. 1994). Immunodepletion of myelin using anti-MAG antibodies removed 63% of its neurite growth inhibition. Together, these findings argue that MAG may inhibit regeneration after injury but this remains controversial. (Bartsch et al. 1995; Schafer et al. 1995) Establishing whether this abundant myelin protein is inhibitory for regeneration of retinal axons would be significant. If so, devising strategies to selectively destroy its activity would provide novel therapies after optic nerve or spinal cord injury.

It is an object of this invention to provide methods that inactivate the inhibitory proteins within myelin and thus promote axon regrowth and regeneration of CNS nerves. It is another object of this invention to provide a method of specifically inactivating myelin-associated glycoprotein and thus promote axon regrowth and regeneration.

SUMMARY OF THE INVENTION

The inventors have discovered that the inactivation of myelin associated glycoprotein (MAG) promotes axon regrowth and regeneration in damaged CNS neurons. In one embodiment, the invention is a method of promoting axon regeneration of a CNS nerve in the tissue of a mammal by specifically inactivating the function of MAG using chromophore-assisted laser inactivation (CALI).

The method of treatment is conducted in a patient as follows, using optic nerve as an example. A damaged optic nerve of a patient is contacted with an anti-MAG antibody having a malachite green chromophore tag, for example by infusing the antibody into the eye or eye cavity using a catheter for a time and under conditions sufficient to allow binding of the antibody to MAG in the myelin of the optic nerve. The optic nerve is then irradiated with a laser beam at a wavelength of 620 nm for a time sufficient to activate the malachite green chromophore tag which tag produces short-lived free radicals that selectively and irreversibly inactivate the function of the MAG bound to the antibody without damage to the tissues of the patient. The turnover time for MAG in myelin is approximately 40 days, thus additional treatment may be required to selectively inactivate the MAG in the myelin of the optic nerve until a time at which axon regeneration is complete.

In a preferred embodiment the method of the invention is directed to axon regeneration any of the following CNS nerves, any of the twelve cranial nerves (such as the optic nerve and auditory nerve), spinal cord and nerves which carry signals into the spinal cord (e.g. sciatic nerve).

DETAILED DESCRIPTION OF THE PREFERRED EMBODIMENTS

The antibodies used in the present invention are prepared by a variety of known methods. Monoclonal antibodies are preferred for use, and such monoclonal antibodies can be prepared in various ways using techniques well understood by those having ordinary skill in the art. For example, monoclonal antibodies can be prepared using hybridoma technology (Kohler, et al., *Nature*, 256:495 (1975); Hammerling, et al., In: *Monoclonal Antibodies and T-Cell Hybridomas*, Elsevier, N.Y., pp. 563–681 (1981)).

Either function blocking or non-function blocking monoclonal antibodies can with the invention, however, use of non-function blocking monoclonal antibodies is preferred. Non-function blocking antibodies facilitate the selectivity of the treatment according to the invention by providing for the inactivation of only those MAG proteins which are at the site of the laser irradiation rather than all MAG proteins in the tissue to which the antibodies bind. In addition in the method of the invention, the antibodies are applied acutely. In a clinical setting, this short exposure is less likely to lead to an inflammatory response against the antibodies, which inflammatory response may disrupt the treatment or otherwise interfere with the treatment of an individual.

Of special interest to the present invention are antibodies which are produced in humans, or a "humanized" (i.e. non-immunogenic in a human) by recombinant or other technology such that they will not be antigenic in humans. Humanized antibodies may be produced, for example by replacing an immunogenic portion of an antibody with a corresponding, but non-immunogenic portion, i.e., chimeric antibodies) as is well understood by those having ordinary skill in the art. General reviews of "humanized" chimeric antibodies are provided by Morrison, S. L. (*Science*, 229:1202–1207 (1985)) and by Oi, et al., (*BioTechniques*, 4:214-ff. (1986)).

The antibodies to MAG are bound to a laser activated chromophore tag. This chromophore tag in turn, when later exposed to laser activation will react in such a manner as to produce free radicals that will inactivate MAG. An example of a chromophore that can be used in the invention is malachite green. The binding of the chromophore tag to the antibodies can be done using standard techniques commonly known to those of ordinary skill in the art. For example, antibodies and other ligands reagents can be labeled with malachite green isothiocyanate (Molecular Probes Inc.) as described in Jay (1988).

The tagged MAG antibodies are administered to a patient at the desired site of treatment according to techniques commonly know n to those of ordinary skill in the art. For example, the tagged MAG antibodies may be infused into the area of the nerve to be treated using a catheter.

In a clinical application the MAG of CNS nerves may be inactivated by introduction of the laser via an optic fiber to the site of lesion according to generally accepted surgical procedures. For example, to treat the optic nerve the laser would be focused on the optic nerve by introduction of the laser light via an optic fiber into the eye cavity or the eyeball itself, depending on the location of the lesion. To treat spinal cord nerves, the laser light would be introduced into the spinal column via the interstices between the vertebrae. The nerve to be treated would then be subjected to laser light at a wavelength that is not absorbed by cellular components and for a time to activate the chromophore tag, e.g. two to five minutes. Inactivation of MAG by CALI results in the specific and irreversible inactivation of each MAG protein that is bound to a labeled antibody when irradiated. Since MAG protein in myelin is replaced, or turns over, approximately every 40 days, the method of the invention would be repeated as many times as is necessary to permit complete axon regeneration.

The method of chromophore-assisted laser inactivation (CALI) will inactivate specific proteins with high spatial and temporal resolution Jay, 1988). CALI can convert "binding reagents" such as antibodies or ligands into function-blockers. It takes advantage of both the specificity inherent in the ligand-receptor interaction and the spatial specificity of the laser activated chromophore tag. For example, a "probe" (which can be a ligand or antibody) is tagged with the dye malachite green (MG) or other chromophore which produces free radicals upon exposure to laser light having a wavelength that is not significantly absorbed by cellular components. The probe is then incubated with the sample of interest. The excess unbound probe need not be washed away due to the spatial specificity of malachite green (half-maximal effect radius =15 Å; Liao et al., 1995). An area of inactivation is selected, and irradiated with a laser beam at a wavelength of 620 nm. This light is absorbed by the malachite green to generate short-lived free radicals that selectively inactivate proteins bound to the MG-labeled probe based on proximity within the laser spot. The laser beam does not cause nonspecific light damage to tissues because the wavelength of light used is not significantly absorbed by cellular components (Jay, 1988; Liao et al., 1994).

As a direct demonstration of its spatial specificity, CALI can inactivate a single subunit of the T cell receptor in living T cells, with only slight effects on nearest neighbors and no effect on other subunits of the multiprotein complex (Liao et al., 1995). CALI has been successfully used to selectively inactivate 40 different proteins (reviewed in Wang and Jay, 1996). Inactivation of proteins by CALI has phenocopied genetic loss of function mutations precisely in all cases tested (n=4) (Schmucker et al., 1994; Schroeder et al. 1996). Further, CALI has been frequently employed with whole embryos to address in vivo function and caused no nonspecific damage to cells or tissue (Jay and Keshishian, 1990; Diamond et al., 1993; Schnucker et al., 1994; Schroeder et al. 1996).

In the specific examples set forth below, CALI is done as described (Jay and Keshishian, 1990; Diamond et al., 1993). CALI is performed with a Nd:YAG driven dye laser using the fluorescent laser dye DCM (Spectra Physics Corp.). It generates a 2 mm spot with 15 mJ per 3 nsec. pulse at a frequency of 10 Hz. Samples are subjected to 2 minutes of laser pulses which has been previously shown to have no nonspecific effect on cells or tissues (Beermann and Jay, 1994).

As used herein, the term "axon regeneration" is defined to mean the growth of an axon from the nerve cell body (soma) through the site of lesion (which lesion can occur by any well known means, e.g., break, cut or crush) to the site innervation thus re-innervating the original target tissue of such nerve. The term "promote" is defined to mean that axon regeneration (i) occurs in an environment where otherwise no axon regeneration would be observed, or (ii) is enhanced, as evidenced by a greater number of axons or greater length of axons.

EXAMPLE 1

CALI of MAG Enhances Retinal Neurite Outgrowth

Dissociated retinal cultures are done as described in Banker and Goslin (1990). The eye is removed from an embryonic day 6 (E6) or embryonic day 7 (E7) chick embryo, as indicated, and the retina dissected away from the surrounding tissues including the pigmented layer. It is then dissociated for 10 minutes at 37° C. in trypsin/EDTA aided by occasional trituration. The cells are pelleted by centrifugation, and resuspended in medium RPMI medium with 10% fetal bovine serum, and penicillin/streptomycin) for plating. The neurons were then plated onto coverslips having the appropriate substrate coating for the indicated experiment and cultured for 20 hours at 37° C., 6% $CO_2$, in Dulbecco's Minimal Eagle's Medium (Gibco) supplemented with 10 fetal bovine serum, 2% chick serum and antibiotics/antimycotics. Retinal ganglion cells can be identified using a specific antibody marker such as 8D9 which recognizes NgCAM.

Using a non-function blocking monoclonal antibody against MAG (anti-MAG antibody INM2C4-3E4), it was demonstrated that CALI of MAG performed on soluble or substrate bound myelin results in the disruption of the inhibitory effects of myelin on retinal neurite outgrowth in culture. The monoclonal antibodies used were specific for MAG as determined by Western blot assays and such antibodies do not by themselves block neurite inhibition (data not shown). Briefly, the experimental protocol is as follows. Glass coverslips are first coated with poly-L-lysine (a neutral substrate used as a positive control for growth), followed by either bovine CNS myelin, or purified MAG (either from bovine or recombinant) on selected coverslips. The myelin or MAG was allowed to adhere to the poly-L-lysine, and the coverslips were washed gently to remove unbound material. Further, a portion of the coverslips coated with myelin or MAG were pre-treated with antibodies, with or without laser irradiation prior to plating the retinal cells. Dissociated E6 retinal cells, prepared as described above, were then plated on these substrates and incubated overnight at 37° C. These cells were observed 20 hours after plating and scored for the presence of neurites.

Figure 3:
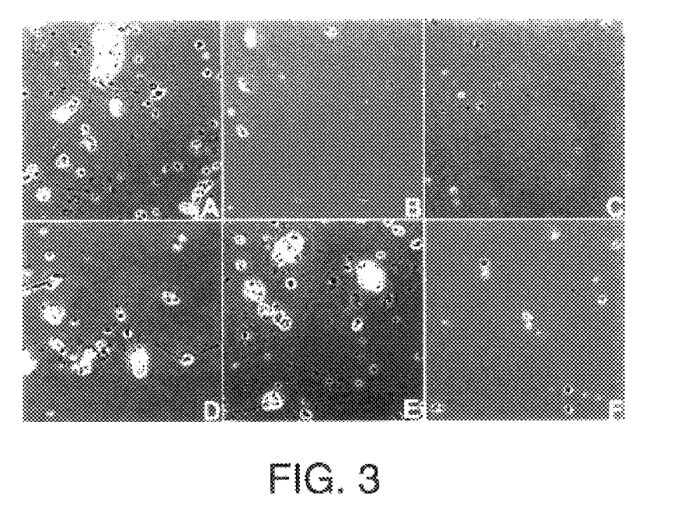
FIG. 3 is a black and white photograph depicting the extension of neurites from dissociated retinal neurons from E7 chick 24 hours after plating such neurites on the following substrates: Panel A, PLL; Panel B, Myelin; Panel C, recombinant MAG, Panel D, MAG-CALI-MAG; Panel E, Myelin-CALI-MAG; or Panel F, Myelin-CALI-MBP (all as defined in Example 1).

The antibodies used were a monoclonal anti-MAG antibody, and monoclonal anti-MBP (myelin basic protein) both of which were labeled with the dye malachite green. MBP is an abundant and well characterized protein in myelin that has not been associated with inhibition and is used as a negative control in these experiments. These antibodies were incubated with the myelin and MAG preparations (2 mg Ab: 5 mg myelin) for 60 minutes at 4° C. Samples subjected to laser inactivation were irradiated with 620 nm laser light with an average energy of 15 mJ/pulse for 5 minutes (total energy =45 J). Briefly, as described above, dissociated retinal neurons from E6 chick were grown on poly-L-lysine (PLL), bovine CNS myelin (Myelin), bovine CNS myelin that has had the MAG inactivated by CALI prior to plating the cells (Myelin-CALI-MAG), purified bovine MAG (MAG), purified bovine MAC that was inactivated by CALI prior to plating the cells (MAG-CALI-MAG), and bovine CNS myelin that was treated with anti-MBP and subjected to CALI (Myelin-CALI-MBP). FIG. 3 is a photograph showing the dissociated retinal neurons grown on each of these substrates. As depicted in FIG. 3, panels A, D, and E, dissociated chick retinal neurons can attach and extend neurites when plated on PLL, MAG-CALI-MAG and Myelin-CALI-MAG, respectively. As depicted in FIG. 3, Panels B, C and F, dissociated chick retinal neurons can attach but neurite extension is significantly inhibited when plated on Myelin, recombinant MAG or Myelin-CALI-MBP. Immunochemistry with anti L1 antibody and retrograde DiI labeling from the optic nerve confirmed the morphological identification of ganglion cells (data not shown).

The cumulative results of three separate experiments under the conditions described above are shown in Table 1, and in FIGS. 1 and 2. The results do not distinguish between the neuronal and nonneuronal cells, therefor the reported number of cells bearing neurites is low even without the inhibitory presence of myelin. In other experiments, 8D9 is used to identify retinal ganglion cell neurites.

Figure 1:
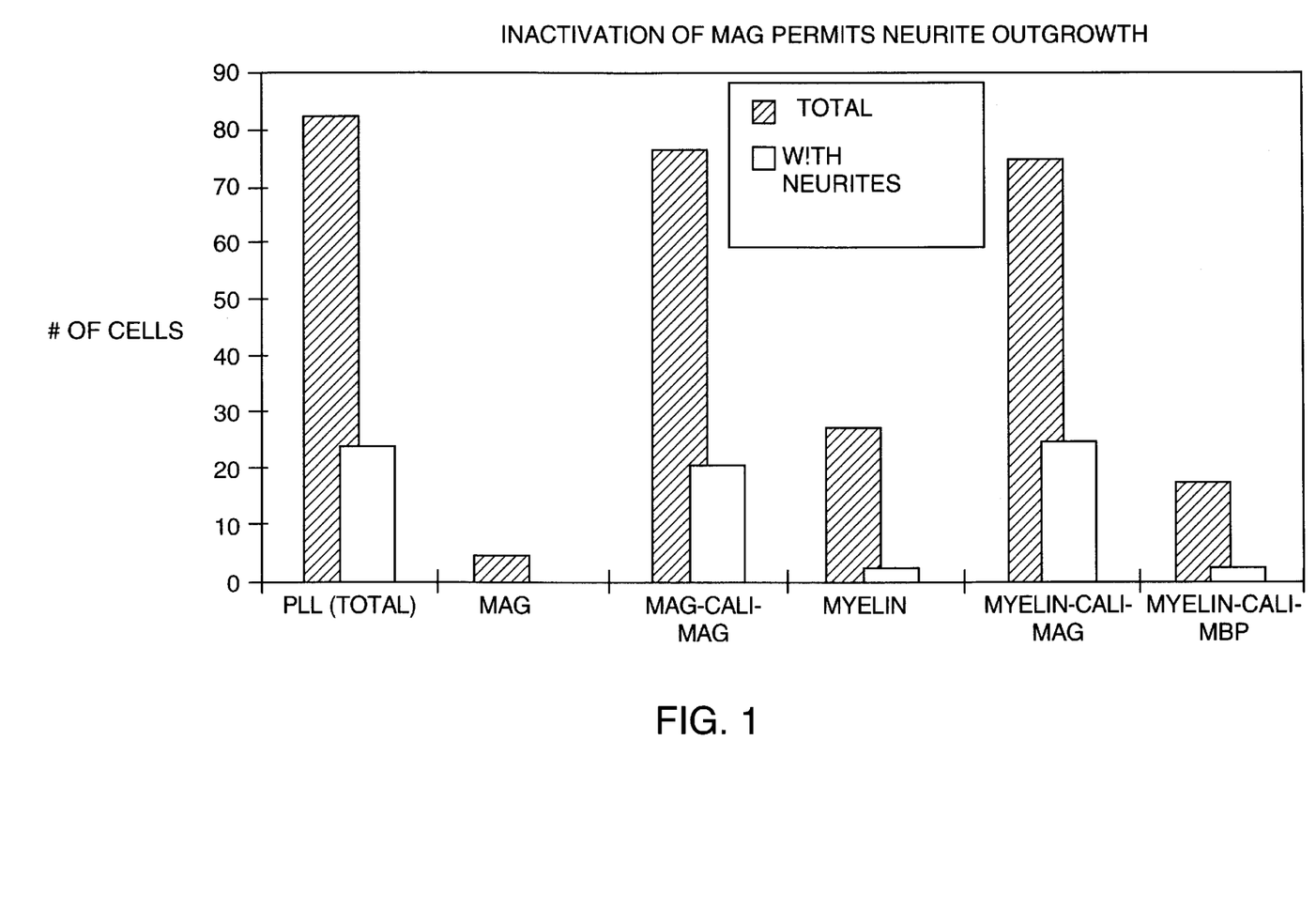
FIG. 1 is a bar graph depicting the total number of cells adherent to the indicated substrates and the number of these adherent cells which have neurite outgrowths.
Figure 2:
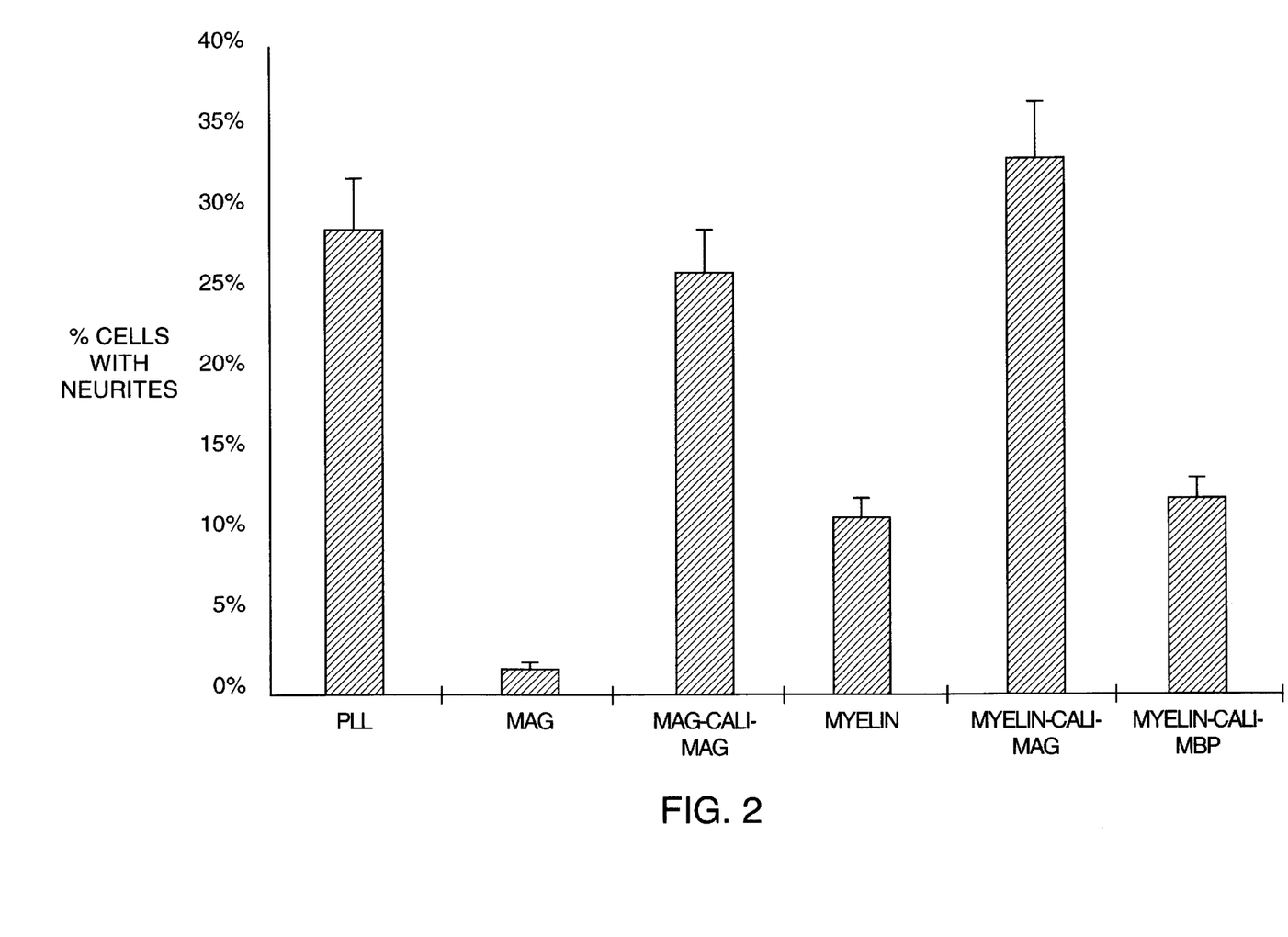
FIG. 2 is a bar graph depicting the percentages of the cells with neurites from the data shown in FIG. 1.

| Substrate | # of adherent cells | Std. Dev. | % of cells with Neurites | Std. Dev. | # of cells with Neurites | Std. Dev. |
|---|---|---|---|---|---|---|
| PLL (total) | 83 | 26 | 29% | 7% | 24 | 8 |
| MAG | 5 | 3 | 0% | 7% | 0 | 1 |
| MAG-CALI-MAG | 77 | 25 | 26% | 10% | 20 | 10 |
| Myelin | 27 | 9 | 11% | 3% | 3 | 2 |
| Myelin-CALI-MAG | 75 | 17 | 33% | 10% | 25 | 14 |
| Myelin-CALI-MBP | 17 | 5 | 12% | 2% | 2 | 1 |

As shown in Table 1, the cells adhere well to PLL, MAG-CALI-MAG and Myelin-CALI-MAG, but do not adhere well to the substrates MAG, Myelin and Myelin-CALI-MBP. As shown in Table 1 above and in FIGS. 1 and 2, inactivation of MAG using CALI, on both the coverslips coated with purified MAG and coverslips coated with myelin, permits neurite outgrowth which is significantly better than that on untreated MAG or myelin, and is similar to the outgrowth observed on the neutral substrate PLL. As CALI of purified MAG permits neurite outgrowth, this treatment affects MAG specifically Additionally, CALI of MAG had no measurable effect on neurite extension as measured by the length of the longest neurite.

These results further demonstrate that CALI of MAG inactivates MAG, and that inactivation of MAG in myelin significantly promotes neurite outgrowth on this substrate.

EXAMPLE 2

CALI of MAG is not Harmful to Retinal Cells in Culture

CALI of MAG was also performed in the presence of the cultured retinal neurons which demonstrated that CALI is not harmful to the cultured retinal cells. CALI of MAG performed on the cultured retinal cells provided similar results as were reported in Example 1. Briefly, chick E6 dissociated retinal cells were plated on poly-L-lysine or myelin. Several 2mm spots of each dish were subjected to 2 minutes of 620 nm laser light in the presence of MG-labeled anti-MAG or MG-labeled nonimmune IgG. The cells were grown for an additional 20 hours, fixed, and stained with anti-tubulin to visualize neurites (data not shown). A comparison of the cells grown under these conditions demonstrated that CALI of MAG on the cultured retinal neurons grown on myelin had enhanced retinal neurite outgrowth when compared to neurons grown on myelin and subjected to CALI of nonimmune IgG, and that CALI had no observable harmful effects on cells.

Additionally, CALI on neurons in culture and whole embryos does not result in nonspecific damage of the tissues (reviewed in Wang and Jay, 1996).

EXAMPLE 3

Effect of MAG on Initiation of Axon Outgrowth and Axon Elongation

In a separate experiment to distinguish between the effects of MAG on initiation as compared to extension, dissociated retinal neurons from E6 chick are grown on PLL and the following reagents are added: purified MAC, heat inactivated MAG, myelin, heat inactivated myelin, CALI of MAG-treated myelin, and purified MAG treated with CALI of MAG. The reagents are added either at the time of neurite initiation (within 30 minutes of plating) or after 12 hours to allow neurites to form. The cultures are incubated for a total of 24 hours, fixed and stained with 8D9 which recognizes NgCAM to visualize retinal neurites. The percentage of cells bearing neurites, neurite number per neuron, and length of the longest neurite per neuron are assayed from three dishes with more than 100 neurons per dish.

A significant decrease in neurite number and neurite length is observed for myelin-treated cultures and a decrease of neurite number but not neurite length is observed for cultured neurons treated with purified MAG. Neuronal cultures incubated with purified MAG treated with CALI are indistinguishable for all parameters from cultures incubated with PLL alone, heat-inactivated myelin, or heat-inactivated MAG. These controls are also indistinguishable from each other. To check specificity of the antibody, immunoblotting of bovine myelin is performed. CALI using anti-MBP (myelin basic protein) is performed as a negative control for these experiments. CALI of MBP does not affect the inhibitory properties of myelin or purified MAG.

EXAMPLE 4

Axon Regrowth in Optic Nerve Explants by Inactivation of MAG using CALI

Organotypic retina/optic nerve culture are done as briefly described below. Retina-optic nerve explants from E7 or embryonic day 13 (E13) chick embryos were dissected in Hanks buffered salt solution (HBSS). The optic nerves were severed at the optic chiasm and left attached to the retina and the pigmented epithelium was dissected away. For E13 retinas, 5 µl of MG-labeled antibody (2 mg/ml in HBSS) was injected into the optic nerve with a Hamilton syringe. The retinae/optic nerve stumps were transferred into DMDEM/ 10% FBS/2% CS/PSF and incubated at 37° C. for 2 hours. The optic nerves were then positioned under the focus of a dye-coupled Nd:YAG laser and irradiated for 3 minutes for a total energy of approximately 30 J. The diameter of the spot is approximately 2 mm wide, and encompassed the entire optic nerve stump. Since the pigment epithelium had been dissected away, the 620 nm wavelength laser light was not absorbed by the retina and had no detectable detrimental effects. After irradiation, the retinae were spread out on a Millicell-CM (Millipore) nitrocellulose filter resting in medium. The retinal ganglion cell layer is facing the filter while the optic nerve stump is oriented upward. This preparation is incubated overnight at 37° C., 5% $CO_2$. A crystal of DiI or FITC-dextran (70kD, fixable) is placed within the optic nerve at the cut end and retrograde transport is allowed to take place during another 24 hour incubation. The cultures are then fixed and observed by fluorescence microscopy.

Inactivation of inhibitory components in myelin should allow the regeneration of a CNS nerve. To demonstrate that inactivation of MAG using CALI will promote the regeneration of CNS nerve, chick optic nerve organotypic culture was used. Optic nerve explants from E7 and E13 chicks were prepared and cultured as described above.

Retinal-optic nerve explants from E7 embryos can regrow from the soma back to the site of lesion because at this stage of development the optic nerve is not myelinated. Retrograde labeling by FITC-dextran, applied to the E7 nerve stump 24 hours after excision, shows brightly labeled RGC soma and axons (FIG. 4, panel a) which labeling is accepted evidence of regrowth to the site of a lesion. However, by E13 the optic nerve has become myelinated, and retrograde labeling by HITC-dextran, applied to the stump 24 hours after excision, shows no fluorescent cells or axons in the retina (FIG. 4, panel b) because the regrowth is inhibited by the CNS myelin.

Figure 4:
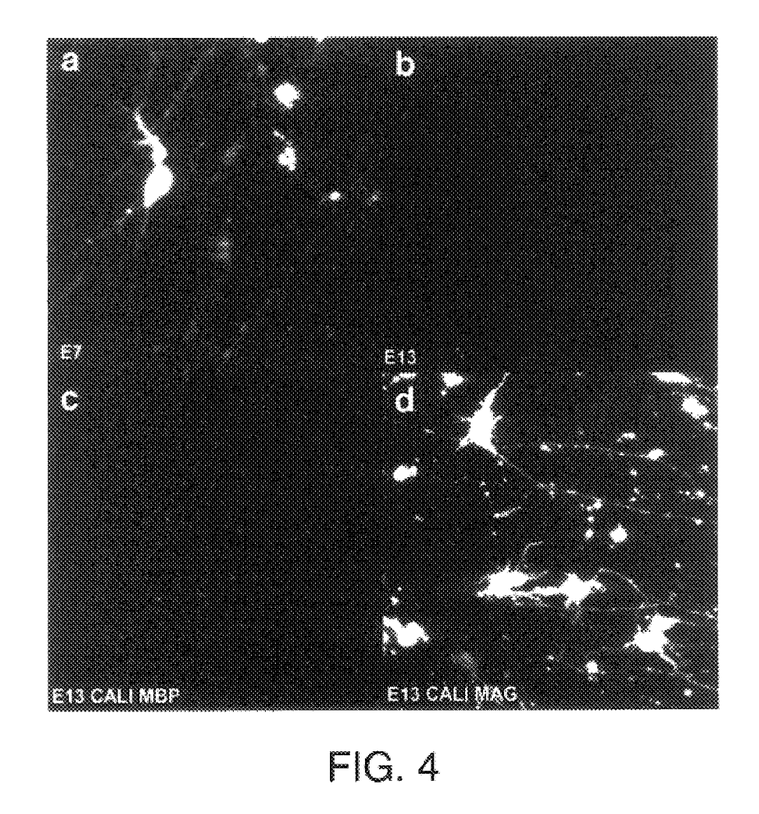
FIG. 4 is a black and white photograph depicting retinal axon regrowth of myelinated optic nerve in embryonic day 7 (E7) and embryonic day 13 (E13) optic nerve explants. Optic nerve stumps were labeled with FITC-dextran for visualization. Depicted are labeled retinas from (a) E7 explants, (b) E13 explants, (c) E13 explants in which MBP was inactivated using CALI of MBP, and (d) E13 explants in which MAG was inactivated using CALI of MAG.

The promotion of axon regeneration by the inactivation of MAG using CALI was demonstrated as follows. E13 optic nerve explants were injected with either MG labeled anti-MAG or MG labeled anti-MBP antibodies immediately after dissection After a 2 hour incubation at 37° C. to allow the antibody to penetrate the tissue and bind the antigen, the optic nerve was subjected to laser irradiation with a 2 mm spot. After overnight incubation, the optic nerve stump was labeled with FITC-dextran and the retinas were examined after an additional 24 hours. As expected E13 optic nerve explants in which CALI was directed against MBP, which protein has not been associated with inhibition of axon regeneration, were observed to have no axon regeneration due to inhibition of regeneration by the myelin (FIG. 4, panel c). Similarly, neither laser irradiation alone of E13 optic nerve explants or treatment of optic nerve explant with monoclonal antibody directed against MAG in the absence of irradiation promoted regeneration of axons in the E13 optic nerve (data not shown). In contrast, the inactivation of MAG using CALI in E13 optic nerve explants was observed to have a significant level of retinal axon regeneration (FIG. 4, panel d). Measurement of the number of fluorescent cell bodies and axons demonstrated that the number of soma labeled in the MAG-inactivated E13 optic nerve explant ($113\pm14$ soma/mm$^2$) was similar to that found in the unmyelinated E7 optic nerve explant ($135\pm13$ soma/mm$^2$). Table 2 is a tabulation of the results with the optic nerve explants. For each sample presented in Table 2, the cells in a 0.2 mm$^2$ field were counted using scanning confocal microscopy, and 12 such fields were counted.

| Age | Treatment | Fluorescent cells/mm$^2$ |
| --- | --- | --- |
| E7 | Control | 135 ± 13 |
| E13 | Control | 0 ± 0 |
| E13 | CALI-MAG | 113 ± 14 |
| E13 | CALI-MBP | 0 ± 0 |

These results demonstrate that MAG has a greater inhibitory effect on axon regeneration than was previously believed by researchers in the field and reported in the literature. In addition, these results with optic nerve explants demonstrate that inhibition of MAG by CALI in myelinated CNS nerve promotes the regeneration of axons. The results described in this Example 3 and in Example 1 using dissociated neurons in culture are indicative of the usefulness of CALI of MAG as a therapeutic method to promote regeneration of axons in vivo.

EXAMPLE 5

Regeneration of Optic Nerve Lesion by Inactivation of MAG by CALI in Optic Nerve Explants The promotion of axon regeneration by inactivation of MAG using CALI was demonstrated as follows. Organotypic retina/optic nerve culture from E13 chick embryos was done as described above except a much longer section of the optic nerve was included (beyond the optic chiasm). A portion of the optic nerve that was proximal to the cut site was subjected to freeze crush which procedure damages the optic nerve axons such that they are no longer able to transmit signals or undergo retrograde labeling. The damaged site of the optic nerve was then treated by CALI of MAG and the regeneration of the optic nerve, from the retina through the area damaged by freeze crush and to the cut site was observed by labeling the cut site using diI (as described above) and fluorescently examining labeled cell bodies within the retina. The results demonstrated that CALI of MAG was able to promote the regeneration of optic nerve axons from the cell bodies in the retina through the damaged area and to the cut site. In the absence of treatment by CALI of MAG, or application of CALI of MBP (a negative control) no regeneration of the axons through the damaged area and to the cut site is observed.

These results demonstrate that treatment of a damage CNS nerve using CALI of MAG promotes axon regeneration.

EXAMPLE 6

Regeneration of Optic Nerve Lesion in Vivo by Inactivation of MAG by CALI

The optic nerve is one of the best characterized CNS fiber tracts. It is relatively homogeneous and accessible to manipulation. Optic nerve lesion is routinely performed in rats and has been used to show that the function blocking mAb IN-1 increases regeneration. However, the regeneration by blocking of IN-1 was incomplete as none of the fibers reached their former targets (Weibel et al., 1994). Weibel et al. also showed a mandatory requirement for BDNF, which factor is readily included by vitreous injection.

The usefulness of CALI of MAG as a therapy to enhance regeneration also is demonstrated using postnatal rat optic nerve lesion. The very slow turnover of myelin proteins, approximately 40 days, makes this a feasible therapeutic strategy. Additionally, CALI of MAG can enhance regeneration alone or may be performed in combination with added IN-1, which is a function-blocking antibody that recognizes a different inhibitory factor in myelin. It is likely the application of multiple therapeutic strategies may be ultimately most effective.

Briefly, analysis of optic nerve regeneration is performed on postnatal day 18 Sprague Dawley rats (modified from Weibel et al., 1994). Aseptic conditions are maintained during surgery and experimental manipulations. Animals are heavily anesthetized by the inhalant anesthetic, Metofane, per manufacturer's suggested protocol. The skull is opened unilaterally over the forebrain. A 1 mm canal is opened in the forebrain by sucking off the tissue with a pipette until the intracranial portion of the right optic nerve is exposed. At the time of lesion, 100 ng of BDNF (Regeneron Inc.) is injected into the vitreous fluid of the right eye. The nerve is lesioned by freeze crush with precooled forceps. Malachite green-labeled anti-MAG, or anti-MBP (100 $\mu$g) in PBS is injected into the lesioned =site and after 4 hours (to allows for antibody accessibility to the MAG proteins), and the site is subjected to 2 minutes of large scale CALI. In some rats, a suspension of hybridoma cells ($5 \times 10^5$ cell in 15 $\mu$l) secreting IN-1 (or anti-HRP as a negative control) is also added. Additional controls include lesion with added dye-labeled reagents without laser light, or lesion without additional manipulation. After treatment, the forebrain canal is filled in with Collastypt and the skull covered with durafilm and histoacryl glue. The eyes are injected with WGA-HRP (1 $\mu$l of 5% solution) 24 hours before sacrifice. Animals are sacrificed at postnatal day 24, and perfused with 1.25% glutaraldehyde, 1% formaldehyde in 0.1 M phosphate buffer. The optic tracts are removed. The optic nerve traces from the left (untreated) and right eyes (treated) are measured by performing complete longitudinal serial sections using HRP histochemistry. Evaluations are done double blind using number coded slides, and axon lengths are measured by darkfield illumination with polarized light with the length of regeneration defined from the border of the lesion on the retinal side.

Intervention is considered promising if CALI of MAG causes a significant increase in axon regeneration as measured by axon length as compared to incubation with anti-MAG alone or laser irradiation with anti-MBP as negative controls (significance tested by Student's t test). Intervention is also deemed successful if there is reconnectivity to former targets, which has not been previously achieved. Combined treatments of CALI of MAG and IN-1 incubation are deemed additive if the extent of regeneration is significantly greater than either treatment alone and are deemed synergistic if the extent of regeneration is significantly greater than the sum of the two.

One of ordinary skill in the art would be aware of, or would be able to determine with no more than routine experimentation, numerous equivalents to the specific methods described herein. Such equivalents are considered to be within the scope of this invention.

The full citation for the references referred to above are set forth below. Each reference is hereby incorporated by reference in its entirety to more fully set forth the state of the art to which this invention pertains.

Aguayo, A. J., Rasminsky, M., Bray, G., M., Carbonetto, S., McKerracher, L., Villegas-Perez, M. P., Vidal-Sanz, M., and Carter, D. A. (1991) Degenerative and regenerative responses of injured neurons in the central nervous system of adult mammals. *Phil. Trans. R. Soc.* (*London*) B 331, 337–343.

Bartsch, U., Bandtlow, C. E., Scnell, L., Bartsch, S., Spillmann, A. A., Rubin, B. P., Hillenbrand, R., Montag, D., Schwab, M. E., and Schachner, M. (1995) Lack of Evidence That Myelin-Associated Glycoprotein Is a Major Inhibitor of Axonal Regeneration in the CNS. *Neuiron* 15, 1375–1381.

Beermann A. E. and Jay, D. G. (1994) Chromophore Assisted Laser Inactivation of Cellular Proteins. *Methods in Cell Biology* 44, 716–732.

Bregman, B. S., Kunkel-Bagden, E. Schnell, L., Dai, H. N., Gao, D., and Schwab, M. E. (1995) Recovery from spinal cord injury mediated by antibodies to neurite growth inhibitors. *Nature* 378, 498–501.

Caroni, P. and Schwab, M. E. (1988a) Two membrane protein fractions from rat central myelin with inhibitory properties for neurite outgrowth and fibroblast spreading. *j. Cell Biol.* 106, 1281–1288.

Caroni, P. and Schwab, M. E. (1988b) Antibody against myelin-associated inhibitor of neurite outgrowth neutralizes nonpermissive substrate properties of CNS white matter. *Neitron* 1, 85–96.

Chang, H. Y., Takei, K., Sydor, A. M., Born, T. Rusnak, F., and Jay, D. G. (1995) Asymmetric retraction of growth cone filopodia follows focal inactivation of calcineurin. *Nature*, 376, 686–690.

Cheng, H., Cao, Y., Olson, L., (1996) Spinal Cord Repair in Adult Paraplegic Rats: Partial Restoration of Hind Limb Function. *Science* 273, 510–512.

Cox, E. C., Muller, B., and Bonhoeffer, F. (1990) Axonal guidance in the chick visual system: posterior tectal membrane induces collapse of growth cones from the temporal retina. *Neuron* 4, 31–37.

David, S. and Aguayo, A. J., (1981) Axonal elongation into peripheral nervous system "bridges" after central nervous system injury in adult rats. *Science* 214, 931–933.

Diamond, P., Mallavarapu, A., Schnipper, J., Booth, J. W., Park, L., O'Connor T. P. and Jay, D. G. (1993) Fasciclin I and II have distinct roles in the development of grasshopper pioneer neurons. *Neuron* 11, 409–421.

Jay, D. G. (1988) Selective destruction of protein function by chromophore-assisted laser inactivation. *Proc. Natl. Acad. Sci.* (*USA*) 85, 5454–5458.

Jay, D. G., and Keshishian, H. (1990) Laser inactivation of Fasciclin-I disrupts axon adhesion of grasshopper pioneer neurons. *Nature* 348, 548–550.

Liao, J. C. Berg, L., and Jay, D. G. (1996) Chromophore-assisted laser inactivation of subunits of the T cell receptor in living cells is spatially restricted. *Photochem. Photobiol.* 62:923–929.

Liao, J. C., Roider, J., and Jay, D. G. (1994) Chromophore-assisted laser inactivation of proteins is mediated by the photogeneration of free radicals. *Proc. Natl. Acad. Sci.* (*USA*) 91, 2659–2663.

McKerracher, L., David, S., Jackson, D. L., Kottis, V., Dunn, R. J., and Braun, P. E. (1994) Identification of Myelin-Associated Glycoprotein as a Major Myelin-Derived Inhibitor of Neurite Outgrowth. *Neuron*, 13, 805–811.

Mukhopadhyay, G., Doherty, P., Walsh, F. S., Crocker, P. R., and Filbin, M. T. (1994) A novel role for myelin-associated glycoprotein as an inhibitor of axonal regeneration. *Neuron*, 13, 757–767.

Muller, B., Jay, D. G., and Bonhoeffer, F. (1996) Chromophore-assisted laser inactivation of a repulsive axonal guidance molecule. *Curr. Biol.* 6, 1497–1502.

Schafer, M., Fruttiger, M., Montag, D., Schachner, M., and Martini, R. (1996) Disruption of the Gene for the Myelin-Associated Glycoprotein Improves Axonal Regrowth along Myelin in C57BL/Wld s Mice. *Neuron* 16, 1107–1113.

Schnell, L. and Schwab, M. E. (1990) Axonal regeneration in the rat spinal cord produced by an antibody against myelin-associated neurite inhibitors. *Neuron* 343, 269–272.

Schroeder, R., Jay, D. G., Tautz, D. (1996) Chromophore-assisted laser inactivation of Drosophila Even Skipped phenocopies genetic loss of function. *Dev. Genes Evol.* 206, 86–88.

Schwab, M. E., Kampfhammer, J. P., and Bandtlow, C. E. (1993) Inhibitors of neurite outgrowth. *Ann. Rev. Neurosci.* 16, 565–595.

Sydor, A. M., Su, A. L., Wang, F. S., Xu, A., and Jay, D. G. (1996) Talin and vinculin functions have distinct roles in filopodial motility in the neuronal growth cone. *J. Cell Biol.* 134, 1197–1208.

Wang, F. S. and Jay, D. G. (1996) CALI and the dissection of growth cone motility *Trends Cell Biol.*, 6, 442–445.

Weibel, D., Cadelli, D., and Schwab, M. E. (1994) Regeneration of lesioned rat optic nerve fibers is improved after neutralization of myelin-associated neurite growth inhibitors. *Brain Res.* 642, 259–266.

We claim:

1. A method of inactivating myelin associated glycoprotein (MAG) in mammalian tissue using chromophore-assisted laser inactivation (CALI) comprising:

(a) exposing MAG to an anti-MAG antibody with a laser activated chromophore tag for a time and under conditions to form a MAG/antibody complex; and (b) irradiating the MAG/antibody complex with a laser beam for a time and under conditions to irradiate the chromophore tag, wherein the irradiated tag selectively inactivates the MAG in the MAG/antibody complex.

2. A method of promoting axon regeneration of a CNS nerve in the tissue of a mammal comprising (a) exposing a damaged CNS nerve to an anti-MAG antibody with a malachite green chromophore tag for a time and under conditions to form a MAG/antibody complex; and (b) irradiating the MAG/antibody complex with a laser beam at a wavelength of 620 nm with an average energy of 15 mJ per 3 nanosecond pulse at a pulse frequency of 10 Hz and for a time sufficient to release free radicals from the chromophore tag, wherein the free radicals inactivate the antibody bound MAG without damage to the tissue.

3. The method of claim 2 wherein the CNS nerve treated is a cranial nerve.

4. The method of claim 3 wherein the CNS nerve treated is an optic nerve.

5. The method of claim 3 wherein the CNS nerve treated is an auditory nerve.

6. The method of claim 2 wherein the CNS nerve treated is within the spinal cord.

* * * * *